United States Patent
Abkai et al.

(10) Patent No.: US 10,052,079 B2
(45) Date of Patent: Aug. 21, 2018

(54) METHOD FOR PRODUCING AN X-RAY IMAGE

(71) Applicant: Sirona Dental Systems GmbH, Bensheim (DE)

(72) Inventors: Ciamak Abkai, Heddesheim (DE); Kai Lindenberg, Wersau (DE)

(73) Assignee: Sirona Dental Systems GMBH, Bensheim (DE)

(*) Notice: Subject to any disclaimer, the term of this patent is extended or adjusted under 35 U.S.C. 154(b) by 0 days.

(21) Appl. No.: 14/905,596

(22) PCT Filed: Jul. 15, 2014

(86) PCT No.: PCT/EP2014/065091
§ 371 (c)(1),
(2) Date: Jan. 15, 2016

(87) PCT Pub. No.: WO2015/007710
PCT Pub. Date: Jan. 22, 2015

(65) Prior Publication Data
US 2016/0166226 A1    Jun. 16, 2016

(30) Foreign Application Priority Data

Jul. 15, 2013    (DE) .................. 10 2013 213 761

(51) Int. Cl.
*A61B 6/00* (2006.01)
*A61B 6/03* (2006.01)
(Continued)

(52) U.S. Cl.
CPC .............. *A61B 6/547* (2013.01); *A61B 6/032* (2013.01); *A61B 6/4435* (2013.01); *A61B 6/501* (2013.01);
(Continued)

(58) Field of Classification Search
CPC ............ A61B 2090/3937; A61B 6/032; A61B 6/0492; A61B 6/4435; A61B 6/501;
(Continued)

(56) References Cited

U.S. PATENT DOCUMENTS 6,243,439 B1    6/2001  Arai et al.
8,559,691 B2   10/2013  Borghese et al.
(Continued)

FOREIGN PATENT DOCUMENTS

DE    10 2008 035 412 A1    2/2010
EP          1 815 794 A1    8/2007
(Continued)

OTHER PUBLICATIONS

Office Action dated Feb. 6, 2014, in German Patent Application No. 10 2013 213 761.3.
(Continued)

*Primary Examiner* — Glen Kao
(74) *Attorney, Agent, or Firm* — Fitzpatrick, Cella, Harper & Scinto

(57) ABSTRACT

The invention relates to a method for producing an x-ray image (1) of an object (2) by means of an x-ray device (3). An x-ray source (4) and an x-ray detector (5) are moved about an object (2) during an at least partial circulation (8, 9), and the x-ray beams (10) which are generated by the x-ray source (4) and pass through the object (2) are detected from multiple different directions by means of the x-ray detector (5). In the process, at least one optical camera (13, 14) captures the object (2) during the circulation, wherein an optical image (15, 17) is produced. The optical camera (13, 14) has a rigidly defined position relative to the x-ray source (4) and/or the x-ray detector (5). The optical image (15, 17)
(Continued)

is then used to determine a movement trajectory of the object (2) relative to the x-ray source (4) and/or the x-ray detector (5).

22 Claims, 1 Drawing Sheet

(51) Int. Cl.
 *A61B 6/04* (2006.01)
 *A61B 90/00* (2016.01)
(52) U.S. Cl.
 CPC ............. *A61B 6/0492* (2013.01); *A61B 6/52* (2013.01); *A61B 6/5294* (2013.01); *A61B 6/584* (2013.01); *A61B 6/589* (2013.01); *A61B 2090/3937* (2016.02)
(58) Field of Classification Search
 CPC ......... A61B 6/52; A61B 6/5294; A61B 6/547; A61B 6/584; A61B 6/589
 See application file for complete search history.

(56) References Cited

U.S. PATENT DOCUMENTS

| | | | |
|---|---|---|---|
| 2007/0183567 | A1 | 8/2007 | Rotondo et al. |
| 2008/0299511 | A1 | 12/2008 | Thoms |
| 2009/0310741 | A1 | 12/2009 | Borghese et al. |
| 2011/0129058 | A1 | 6/2011 | Ulrici et al. |
| 2011/0194670 | A1 | 8/2011 | Borghese et al. |
| 2016/0296292 | A1* | 10/2016 | Ekin ................... A61B 90/361 |
| 2017/0035374 | A1* | 2/2017 | Schafer ................. A61B 6/02 |

FOREIGN PATENT DOCUMENTS

| | | |
|---|---|---|
| EP | 2 130 491 A1 | 12/2009 |
| EP | 2 146 321 A1 | 1/2010 |
| JP | H04-226641 A | 8/1992 |
| JP | H11-253433 A | 9/1999 |
| JP | 2008-510535 A | 4/2008 |
| JP | 2008-161234 A | 7/2008 |
| JP | 2010-148676 A | 7/2010 |
| JP | 2011-529359 A | 12/2011 |

OTHER PUBLICATIONS

Matthias M. Mitschke, Recovering Projection Geometry: How a Cheap Camera Can Outperform an Expensive Stereo System, 2000 IEEE.
International Preliminary Report on Patentability dated Jan. 19, 2016, in International Appln. No. PCT/EP2014/065091.
Written Opinion of the Intl. Search Authority in International Appln. No. PCT/EP2014/065091, 2016.
Intl. Search Report in International Appln. No. PCT/EP2014/065091, 2016.
English translation dated Jan. 30, 2018 Office Action in Japanese Patent Application No. 2016-526575.

\* cited by examiner

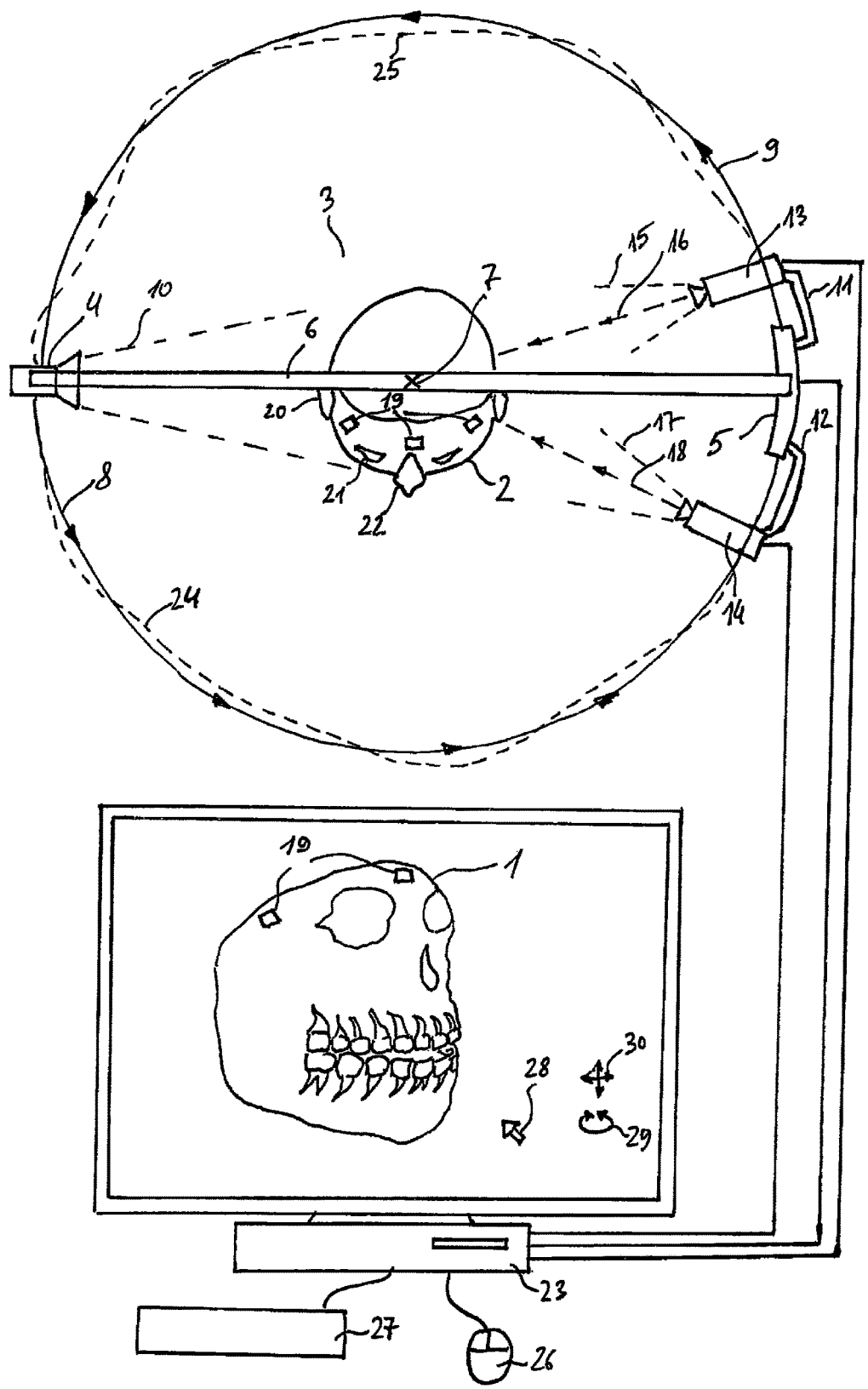

METHOD FOR PRODUCING AN X-RAY IMAGE

TECHNICAL FIELD

The invention relates to a method for creating an x-ray image of an object by means of an x-ray device, wherein during one at least partial circulation, an x-ray source and an x-ray detector are moved around an object, wherein the x-ray beams generated by the x-ray source and passing through the object are detected from multiple different directions by the x-ray detector.

PRIOR ART

Several methods for creating x-ray images are known from the prior art, wherein an x-ray source and an x-ray detector are moved around an object. During one circulation, two-dimensional x-ray images of the object are created from various directions and then, using a reconstruction method, a three-dimensional x-ray image or a panoramic tomographic image of the object is calculated from the two-dimensional x-ray images.

EP 2146321 A1 discloses an x-ray device having an x-ray source and an x-ray detector which are moved around an object, wherein the object is recorded by means of a camera. The camera is set up outside of the x-ray device and is not rotated with it. The optical images of the object made by the camera are then used to compensate for movements of the object while the x-ray image is being recorded.

One disadvantage of this method is that a deformation of the carrying arm or a movement trajectory of the object relative to the carrying arm while recording an image can lead to image errors. To correct these image errors, there is a known method in which a calibration of the x-ray device is performed by means of a calibration phantom before each x-ray image. Changes in the circulation trajectory, which may for example be caused by mechanical deformation of the carrying arm or the bearings used, for example, are ascertained.

The object of the present invention is thus to make available a method for creating an x-ray image which will easily permit an error-free three-dimensional x-ray image without prior calibration measurements.

DESCRIPTION OF THE INVENTION

The invention relates to a method for generating an x-ray image of an object by means of an x-ray device, wherein during one at least partial circulation, an x-ray source and an x-ray detector are moved around an object, wherein the x-ray beams created by the x-ray source and passing through the object are detected from several different directions by means of the x-ray detector. At least one optical camera records the object during the circulation, and at least one first optical image is created, wherein the optical camera has a known and defined positional relationship to the x-ray source and/or to the x-ray detector. The optical image recording is then used to determine a movement trajectory of the object relative to the x-ray source and/or to the x-ray detector.

The x-ray recording method may be either a three-dimensional x-ray recording method such as DVT or CT, or a two-dimensional x-ray recording method such as a panoramic tomographic image.

In the so-called digital volume tomography method (DVT) or in so-called computer tomography (CT), the x-ray source and the x-ray detector are moved around the object, such as a patient's head, wherein two-dimensional projection images are created from different directions, a three-dimensional volume being calculated from these projection images in the next step. This calculated three-dimensional x-ray image can then be displayed in user software by means of a display device such as a display screen. The imaging is thus based on a continuous recording of the projection from different directions, wherein the three-dimensional x-ray image is calculated by using a reconstruction method, the respective x-ray absorption values being assigned to the so-called voxels of the three-dimensional x-ray image.

In a panoramic tomographic image, the x-ray source and the x-ray detector are also moved around the object, wherein a sharp layer having a blurring component is formed. Due to the change in the circulating trajectory of the x-ray source and the x-ray detector, the sharp layer can be adapted to the object to be recorded accordingly.

The x-ray source and the x-ray detector may be mounted on a carrying arm, for example. The carrying arm may have bearings and drive means, wherein drive means such as an electric motor can be controlled such that the x-ray source and the x-ray detector are moved along the planned trajectory around the object. In a DVT method or a CT method, the trajectory of the x-ray source and of the x-ray detector may be circular.

The optical camera may be any digital video camera which records the object continuously during the entire circulation. The optical camera has a defined positional relationship to the x-ray source and/or to the x-ray detector, so that the deformation of the carrying arm and/or a relative movement of the object can be determined. The deformation of the carrying arm can be generated by an external load on the carrying arm, for example, or by vibrations caused by drive means of the carrying arm during operation.

The optical camera has a known and defined positional relationship to the x-ray source and/or to the x-ray detector. The optical camera may thus be mounted on the x-ray source and/or on the x-ray detector, for example. Alternatively, the optical camera may also be mounted on a movable rail which is moved in a defined manner relative to the x-ray source and/or to the x-ray detector during the circulation. The position and orientation of the optical camera relative to the x-ray source and/or to the x-ray detector are thus known at each point in time during the measurement.

The movement trajectory of the object thus defines the time-dependent position and orientation of the object relative to the x-ray source and/or to the x-ray detector during the circulation.

The object, such as a patient's head, need not be secured but instead may be moved freely relative to the carrying arm during the circulation within a recording volume of the x-ray device.

One advantage of this method is that calibration by means of a calibration phantom is no longer necessary before each measurement because the relative movement trajectory is ascertained directly during the measurement by means of the optical camera. A so-called online calibration is thus performed during the measurement.

Another advantage of this method is that the object, such as a patient's head, need not be secured relative to the x-ray device, as is the case with traditional methods using fixation means such as a bite piece and/or a supporting surface. The patient can thus move freely within the image volume within the defined tolerance limits.

In calculation and/or reconstruction of the three-dimensional x-ray image from the individual two-dimensional x-ray images, the deformation of the carrying arm and the movement trajectory of the object are thus taken into account in relation to the x-ray source and/or to the x-ray detector.

However, the x-ray source and the x-ray detector may also have different carrying arms and drive means so that they can be moved around the object independently of one another. A first optical camera can be mounted on the x-ray source, ascertaining a first movement trajectory of the x-ray sources, and a second optical camera can be mounted on the x-ray detector, ascertaining a second movement trajectory of the x-ray detector.

As an alternative to that, the first optical camera can be mounted laterally on the x-ray source and/or on the x-ray detector by means of a holder such that the camera at least partially records both the object and the opposing x-ray detector and the opposing x-ray source, so that the first movement trajectory of the x-ray source and the second movement trajectory of the x-ray detector can be determined from the first optical image by means of the first optical camera, and a second optical camera is not necessary.

The at least one optical image may advantageously be used to determine movements of the object relative to the x-ray source and/or the x-ray detector during the circulation.

Thus, the movement trajectory of the object is determined.

The x-ray source and the x-ray detector can advantageously be mounted fixedly on a carrying arm, wherein the optical image is used to additionally determine a deformation of the carrying arm during the circulation.

Therefore, in calculation and/or reconstruction of the three-dimensional x-ray image, the deformation of the carrying arm and the movement trajectory of the object relative to the x-ray source and/or the x-ray detector are to be taken into account so that possible imaging errors can be minimized.

The optical camera can advantageously be mounted on the x-ray source, on the x-ray detector and/or on the carrying arm.

The position of the optical camera relative to the x-ray source, to the x-ray detector and/or to the carrying arm is therefore fixed.

The movement trajectory of the object ascertained relative to the x-ray source and/or to the x-ray detector can advantageously be used to calculate a three-dimensional x-ray image from a plurality of two-dimensional x-ray images detected from different directions by means of the x-ray detector.

Therefore, using the reconstruction method, an error-free three-dimensional image can be calculated, taking into account the actual movement trajectory ascertained and not just a planned or calibrated deviating movement trajectory, such as that with traditional CT x-ray devices.

In addition to the first optical camera, a second optical camera can advantageously also record the object during the circulation, wherein a second optical image of the object is created, the two optical cameras having a known and defined positional relationship to one another.

The second optical camera may be any optical digital video camera which records the object from a second recording direction during the circulation. The determination of the position of the object relative to the carrying arm is therefore improved.

The optical marks can advantageously be applied to the object and can be detected by means of the optical camera.

The optical marks may have structures which are uniquely recognizable optically, for example. The optical marks may have an adhesive film so that they can be applied to the object, such as a patient's head.

The optical marks are then detected in the optical images of the optical camera so that the change in position of the object during the entire circulation can be determined in relation to the x-ray source and/or to the x-ray detector.

Prominent structures of the object, such as the ear, the lips, the chin or the eyes of a patient's head, can be determined advantageously in order to determine the positional relationship of the object relative to the carrying arm.

The change in position of the object can therefore also be tracked on the basis of the prominent structures of the object during the circulation.

The optical marks on the object and/or the prominent structures of the object can advantageously be detected by using pattern recognition algorithms in the optical image.

When using pattern recognition algorithms, matching regions are detected in the optical video images and then used for determining the positional change in the object. The corresponding regions may have prominant structures such as the ear, lips, chin or eyes of the patient's head.

Image errors can advantageously be corrected in the calculation of the three-dimensional x-ray image in that a planned ideal trajectory of the circulation is replaced by the actual movement trajectory ascertained by means of the optical camera, wherein the actual movement trajectory takes into account the deformation of the carrying arm and/or the relative positional trajectory of the object during the circulation.

In the software for calculation and/or reconstruction of the three-dimensional x-ray image, the planned ideal trajectory is therefore replaced by the actual trajectory measured by means of the optical camera. A traditional x-ray device can be modified easily in this way according to the present method by mounting at least one optical camera on the x-ray source, on the x-ray detector and/or on the carrying arm, and replacing only the movement trajectory in the pre-existing software.

BRIEF DESCRIPTION OF THE DRAWINGS

The invention will be explained with reference to the drawings. In the FIGURE:

FIG. 1 shows a diagram illustrating the method for generating a three-dimensional x-ray image.

EXEMPLARY EMBODIMENT

FIG. 1 shows a diagram illustrating the method for generating a three-dimensional x-ray image 1 of an object 2 such as a patient's head by means of an x-ray device 3. The x-ray device 3 comprises an x-ray source 4 and an x-ray detector 5 arranged on opposite ends of a carrying arm 6. The carrying arm 6 is mounted in the x-ray device 3 such that the carrying arm 6 rotates with the x-ray source 4 and the x-ray detector 5 around a common axis of rotation 7 which is represented as a cross. During one at least partial circulation, the x-ray source 4 is rotated along a first ideal trajectory 8, which is represented as a continuous line with arrows, and the x-ray detector 5 is rotated along a second ideal trajectory 9. In the present exemplary embodiment, the first ideal trajectory 8 and the second ideal trajectory 9 are circular. The x-ray source 4 generates x-ray beams 10, which pass through the object 2 and are detected by means of the x-ray detector 5 during the circulation. Two-dimensional x-ray images of the object 2 are created from different recording directions in this way and are then used to calculate the three-dimensional x-ray image 1 by reconstruction. In addition, a first optical camera 13 and a second optical camera 14 are mounted on the x-ray detector 5 by means of the holders 11 and 12. Alternatively, the optical cameras 13 and 14 can also be mounted directly on the carrying arm 6 or on the x-ray source 4. The optical cameras 13 and 14 are traditional optical digital video cameras. The first optical camera 13 records a first optical image 15 of the object 2 from a first recording direction 16 during the circulation, while the second optical camera 14 records a second optical image 17 from a second recording direction 18. The first recording direction 16 and the second recording direction 18 of the two optical cameras 13 and 14 form an angle of approximately 30° to one another so that the change in position of the object 2 relative to the carrying arm 6 and thus relative to the x-ray source 4 mounted thereon and the x-ray detector 5 can be determined. Optical marks 19, which are adhered to the forehead region of the patient's head 2, are used for determining the positional relationship of the object 2 relative to the carrying arm 6. In the present exemplary embodiment, the optical marks 19 are designed rectangular and can be detected by means of the optical cameras 13 and 14 to determine the exact positional relationship between the patient's head 2 and the carrying arm 6 and the x-ray detector 5. Alternatively or additionally, characteristic structures of the patient's head 2 such as the ears 20, the eyes 21 and the nose 22 can be used to determine the positional relationship. The marks 19 as well as the characteristic structures 20, 21 and 22 can be recognized by using known pattern recognition algorithms in the optical images 15 and 17. The image data of the two optical cameras 13 and 14 as well as the image data of the x-ray detector 5 are transmitted to a computer 23, wherein the computer 23 performs the calculation of the three-dimensional x-ray image 1 by reconstruction from the individual two-dimensional x-ray images from different recording directions, wherein the two optical images 15 and 17 during circulation from the different recording directions 16 and 18 are used to perform a correction. In these correction methods, the measured positional relationship between the x-ray detector 5 and the object 2 is taken into account so that recording errors, which are caused by deformation of the carrying arm during circulation and/or due to a change in position of the object 2 during circulation relative to the carrying arm 6, are corrected. This correction method can be carried out by means of the computer 23 in the employed software in that a first actual movement trajectory 24 of the x-ray source 4 and the second actual movement trajectory 25 of the x-ray detector 5, which are shown with broken lines, are used to calculate the three-dimensional x-ray image instead of using the planned ideal trajectories 8 and 9. The first actual trajectory 24 and the second actual trajectory 25 are sketched for the sake of illustration. The two actual movement trajectories 24 and 25 are shaped so that they take into account deformation of the carrying arm 6 and the relative change in position of the object 2 during the circulation. Therefore, the same software as in a traditional x-ray device can be used, with only the ideal trajectories 8 and 9 being replaced by the corrected actual trajectories 24 and 25. The user can navigate in the three-dimensional x-ray image 1 by using input means, such as a mouse 26 and a keyboard 27, using a virtual cursor 28. The user can use one virtual navigation tool 29 for rotation of the three-dimensional x-ray image 1, and a second virtual navigation tool 30 for shifting the three-dimensional x-ray image 1. The marks 19 may also be radiosensitive so that they are visible in the three-dimensional x-ray image 1.

As an alternative, the x-ray source 4 and the x-ray detector 5 can be moved independently of one another by different drive means along any movement trajectories which are determined by using a first optical camera on the x-ray source and a second optical camera on the x-ray detector.

LIST OF REFERENCE NUMERALS

1 x-ray image
2 object
3 x-ray device
4 x-ray source
5 x-ray detector
6 carrying arm
7 axis of rotation
8 first ideal trajectory
9 second ideal trajectory
10 x-ray beams
11 holder
12 holder
13 first camera
14 second camera
15 first image
16 first image direction
17 second image
18 second image direction
19 mark
20 ears
21 eyes
22 nose
23 computer
24 first actual trajectory
25 second actual trajectory
26 mouse
27 keyboard
28 cursor
29 first navigation tool
30 second navigation tool

The invention claimed is:
1. An x-ray imaging method, comprising:
   causing an x-ray source and an x-ray detector to move about an object to a plurality of different positions;
   generating a two-dimensional x-ray image of the object at each of the plurality of different positions;
   generating a plurality of optical images of the object using an optical camera during the movement of the x-ray source and the x-ray detector about the object;
   determining a movement trajectory of the object relative to the x-ray detector based on the plurality of optical images; and
   calculating a three-dimensional x-ray image of the object based on the plurality of two-dimensional x-ray images and the movement trajectory of the object relative to the x-ray detector.
2. The method according to claim 1, further comprising:
   determining a deformation of a carrying arm, on which the x-ray source and the x-ray detector are mounted, that occurs during the movement of the x-ray source and the x-ray detector about the object based on the plurality of optical images,
   wherein the deformation of the carrying arm is used in the determining of the movement trajectory of the object relative to the x-ray detector.
3. The method according to claim 1, wherein the optical camera has a known positional relationship to the x-ray source and/or to the x-ray detector.

4. The method according to claim 1, further comprising:
generating another plurality of optical images of the object using another optical camera during the movement of the x-ray source and the x-ray detector about the object; and
determining a movement trajectory of the object relative to the x-ray source based on the other plurality of optical images,
wherein the three-dimensional x-ray image of the object is further calculated, in the calculating, based on the movement trajectory of the object relative to the x-ray source.

5. The method according to claim 4, wherein the other optical camera has a known positional relationship to the optical camera.

6. The method according to claim 1, further comprising:
detecting one or more prominent structures of the object in each of the plurality of optical images; and
determining, for each of the plurality of different positions, a positional relationship of the object relative to the x-ray source or to the x-ray detector based on the one or more prominent structures detected in a corresponding optical image, and
wherein the positional relationships of the object relative to the x-ray source or to the x-ray detector at the plurality of positions are used in the determining of the movement trajectory of the object relative to the x-ray detector.

7. The method according to claim 1, further comprising:
detecting one or more optical marks on the object in each of the plurality of optical images;
determining, for each of the plurality of different positions, a positional relationship of the object relative to the x-ray source or to the x-ray detector based on the one or more optical marks detected in a corresponding optical image,
wherein the positional relationships of the object relative to the x-ray source or to the x-ray detector at the plurality of positions are used in the determining of the movement trajectory of the x-ray detector relative to the object.

8. A dental imaging system, comprising:
an x-ray source constructed to emit x-ray beams towards an object;
an x-ray detector constructed to detect x-ray beams, wherein the x-ray source and the x-ray detector are configured to move about the object and generate a plurality of two-dimensional x-ray images respectively corresponding to a plurality of different positions;
an optical camera configured to generate a plurality of optical images of the object during the movement of the x-ray source and the x-ray detector about the object; and
a computer configured to:
determine a movement trajectory of the object relative to the x-ray detector based on the plurality of optical images of the object generated by the optical camera during the movement of the x-ray source and the x-ray detector about the object, and
calculate a three-dimensional x-ray image of the object based on the plurality of two-dimensional x-ray images and the movement trajectory of the object relative to the x-ray detector.

9. The dental imaging system according to claim 8, wherein the computer is further configured to:
determine a deformation of a carrying arm, on which the x-ray source and the x-ray detector are mounted, that occurs during the movement of the x-ray source and the x-ray detector about the object based on the plurality of optical images,
wherein the deformation of the carrying arm is used to determine the movement trajectory of the object relative to the x-ray detector.

10. The dental imaging system according to claim 8, wherein the optical camera has a known positional relationship to the x-ray source and/or to the x-ray detector.

11. The dental imaging system according to claim 8, further comprising:
another optical camera configured to generate another plurality of optical images of the object during the movement of the x-ray source and the x-ray detector about the object,
wherein the computer is further configured to:
determine a movement trajectory of the object relative to the x-ray source based on the other plurality of optical images, and
calculate the three-dimensional x-ray image of the object based on the movement trajectory of the object relative to the x-ray source.

12. The dental imaging system according to claim 11, wherein the other optical camera has a known positional relationship to the optical camera.

13. The dental imaging system according to claim 8, wherein the computer is further configured to:
detect one or more prominent structures of the object in each of the plurality of optical images, and
determine, for each of the plurality of different positions, a positional relationship of the object relative to the x-ray source or to the x-ray detector based on the one or more prominent structures detected in a corresponding optical image,
wherein the positional relationships of the object relative to the x-ray source or to the x-ray detector at the plurality of positions are used by the computer to determine the movement trajectory.

14. The dental imaging system according to claim 8, wherein the computer is further configured to:
detect one or more optical marks on the object in each of the plurality of optical images, and
determine, for each of the plurality of different positions, a positional relationship of the object relative to the x-ray source or to the x-ray detector based on the one or more optical marks detected in a corresponding optical image, and
wherein the positional relationships of the object relative to the x-ray source or to the x-ray detector at the plurality of positions are used by the computer to determine the movement trajectory.

15. A dental imaging apparatus, comprising:
a computer configured to:
receive a plurality of two-dimensional x-ray images of an object generated during a movement of an x-ray source and an x-ray detector about the object, wherein the plurality of two-dimensional x-ray images respectively correspond to a plurality of different positions,
receive a plurality of optical images from an optical camera of the object generated during the movement of the x-ray source and the x-ray detector about the object,
determine a movement trajectory of the object relative to the x-ray detector based on the plurality of optical images, and calculate a three-dimensional x-ray image of the object based on the plurality of two-dimensional x-ray images and the movement trajectory of the object relative to the x-ray detector.

16. The dental imaging apparatus according to claim 15, wherein the computer is further configured to:
   determine a deformation of a carrying arm, on which the x-ray source and the x-ray detector are mounted, during the movement of the x-ray source and the x-ray detector about the object based on the plurality of optical images,
   wherein the deformation of the carrying arm is used to determine the movement trajectory of the object relative to the x-ray detector.

17. The dental imaging apparatus according to claim 15, wherein the optical camera has a known positional relationship to the x-ray source and/or to the x-ray detector.

18. The dental imaging apparatus according to claim 15, further comprising:
   another optical camera configured to generate another plurality of optical images of the object during the movement of the x-ray source and the x-ray detector about the object,
   wherein the computer is further configured to:
      determine a movement trajectory of the object relative to the x-ray source based on the other plurality of optical images, and
      calculate the three-dimensional x-ray image of the object based on the movement trajectory of the object relative to the x-ray source.

19. The dental imaging apparatus according to claim 18, wherein the other optical camera has a known positional relationship to the optical camera.

20. The dental imaging apparatus according to claim 15, wherein the computer is further configured to:
   detect one or more prominent structures of the object in each of the plurality of optical images, and
   determine, for each of the plurality of different positions, a positional relationship of the object relative to the x-ray source or to the x-ray detector based on the one or more prominent structures detected in a corresponding optical image,
   wherein the positional relationships of the object relative to the x-ray source or to the x-ray detector at the plurality of positions are used by the computer to determine the movement trajectory.

21. The dental imaging apparatus according to claim 15, wherein the computer is further configured to:
   detect one or more optical marks on the object in each of the plurality of optical images, and
   determine, for each of the plurality of different positions, a positional relationship of the object relative to the x-ray source or to the x-ray detector based on the one or more optical marks detected in a corresponding optical image, and
   wherein the positional relationships of the object relative to the x-ray source or to the x-ray detector at the plurality of positions are used by the computer to determine the movement trajectory.

22. A non-transitory computer readable storage medium storing program instructions that when executed cause a computer to:
   receive a plurality of two-dimensional x-ray images of an object generated during a movement of an x-ray source and an x-ray detector about the object, wherein the plurality of two-dimensional x-ray images respectively correspond to a plurality of different positions,
   receive a plurality of optical images of the object generated during the movement of the x-ray source and the x-ray detector about the object,
   determine a movement trajectory of the object relative to the x-ray detector based on the plurality of optical images, and
   calculate a three-dimensional x-ray image of the object based on the plurality of two-dimensional x-ray images and the movement trajectory of the object relative to the x-ray detector.

\* \* \* \* \*